United States Patent
Giménez Carol et al.

(10) Patent No.: US 8,322,855 B2
(45) Date of Patent: Dec. 4, 2012

(54) METHOD FOR DETERMINING THE VISUAL BEHAVIOUR OF A PERSON

(75) Inventors: Antonia Giménez Carol, Barcelona (ES); Carmen Prieto Pin, Barcelona (ES); Juan Carlos Dursteler López, Barcelona (ES); Josep Salvador Solaz Sanahuja, Valencia (ES); Begoña Mateo Martinez, Valencia (ES); Rosa Maria Porcar Seder, Valencia (ES)

(73) Assignee: INDO Internacional S.A., Barcelona (ES)

( * ) Notice: Subject to any disclaimer, the term of this patent is extended or adjusted under 35 U.S.C. 154(b) by 674 days.

(21) Appl. No.: 11/568,767

(22) PCT Filed: May 5, 2005

(86) PCT No.: PCT/ES2005/000245
§ 371 (c)(1),
(2), (4) Date: Nov. 6, 2006

(87) PCT Pub. No.: WO2005/107576
PCT Pub. Date: Nov. 17, 2005

(65) Prior Publication Data
US 2007/0229761 A1    Oct. 4, 2007

(30) Foreign Application Priority Data
May 6, 2004    (ES) .................................. 200401161

(51) Int. Cl.
*A61B 3/00*    (2006.01)
*A61B 3/14*    (2006.01)
(52) U.S. Cl. ........................................ 351/209; 351/200
(58) Field of Classification Search .................. 351/200, 351/205, 209, 211, 222
See application file for complete search history.

(56) References Cited

U.S. PATENT DOCUMENTS
4,656,590 A    4/1987    Ace
(Continued)

FOREIGN PATENT DOCUMENTS
EP    0269069    6/1988
(Continued)

OTHER PUBLICATIONS

Pierre Devie, Christine Jouvanceau, Varilux Ipseo eye/head strategy and physiological personalisation; Product/Producto, p.d.v. No. 49, Autumn 2003, pp. 23-27.
(Continued)

*Primary Examiner* — Joseph P Martinez
*Assistant Examiner* — Brandi Thomas
(74) *Attorney, Agent, or Firm* — Peter B. Scull; Hamilton, DeSanctis & Cha, LLP

(57) ABSTRACT

The invention relates to a method and device for determining the visual behavior of a person. The inventive method comprises the following steps consisting in: recording the movement of the individual's head, recording the movement of his/her eyes, determining the relative orientation of the eye in relation to the head, and determining the amount of time for which the eye is maintained in each orientation. The aforementioned amount of time is determined by collecting the records of orientations in finite intervals and counting the number of records (frequency) in each interval. Said orientations are specified using angular co-ordinates for both the head and the eye. The data are detected and processed with the aid of a device comprising light emitters (51) which are fixed to the head, cameras (63) and a screen (611, 612) for attracting the individual's gaze. The results from the method are used in order to customize the design of a lens for spectacles.

11 Claims, 5 Drawing Sheets

U.S. PATENT DOCUMENTS

| | | |
|---|---|---|
| 5,345,281 A | 9/1994 | Taboada et al. |
| 6,089,713 A | 7/2000 | Hof et al. |
| 6,199,973 B1 | 3/2001 | Bartolome et al. |
| 6,419,549 B2 | 7/2002 | Shirayanagi |
| 6,574,352 B1 * | 6/2003 | Skolmoski .................. 382/103 |
| 6,827,443 B2 | 12/2004 | Fisher et al. |
| 7,460,940 B2 * | 12/2008 | Larsson et al. .................. 701/49 |
| 2003/0117578 A1 | 6/2003 | Haimerl |
| 2003/0156251 A1 | 8/2003 | Welk et al. |

FOREIGN PATENT DOCUMENTS

| | | |
|---|---|---|
| EP | 0759722 | 3/1997 |
| EP | 1087252 | 3/2001 |
| EP | 1154302 | 11/2001 |
| EP | 1261273 | 12/2002 |
| EP | 0888004 | 2/2006 |
| FR | 2753805 | 3/1998 |
| FR | 2863857 | 6/2005 |
| JP | 03206417 | 9/1991 |
| JP | 10115808 | 5/1998 |
| WO | 01/62139 | 8/2001 |
| WO | 03/048841 | 6/2003 |
| WO | 03/052491 | 6/2003 |
| WO | 2005/070284 | 8/2005 |

OTHER PUBLICATIONS

Pierre Simonet, Thierry Bonnin, et al., Eye/Head coordination in presbyopes; Technical File/Expediente Tecnico, p.d.v. No. 49, Autumn 2003, pp. 17-22.

* cited by examiner

METHOD FOR DETERMINING THE VISUAL BEHAVIOUR OF A PERSON

CROSS-REFERENCE TO RELATED APPLICATIONS

The present application is the US national stage application of the Patent Cooperation Treaty (PCT) Application Number PCTIES 2005/000245, filed 5 May 2005, entitled "METHOD AND DEVICE FOR DETERMINING THE VISUAL BEHAVIOUR OF A PERSON AND METHOD OF CUSTOMISING A SPECTACLE LENS"; which designated all states including the United States of America; the subject matter of which hereby being specifically incorporated herein by reference for all that it discloses and teaches; and claims priority from the Spanish Patent Application, Number P200401161, filed 6 May 2004, the subject matter of which also hereby being specifically incorporated herein by reference for all that it discloses and teaches.

The invention relates to a method for establishing the visual behaviour of a person which comprises the step of recording the movement of his/her head while performing a visual task, and to an equipment comprising a device for sensing the movement of the individual's head while performing a visual task. It also refers to a method of customisation of a lens for spectacle frame comprising the step of establishing the visual behaviour of the lens wearer while performing a visual task.

BACKGROUND OF THE INVENTION

It is relatively frequent that persons older than forty years suffer from presbyopia, or farsightedness, meaning that his/her eyes lose the focus ability at different distances, and appearing especially in vision loss at short distances.

Customarily, presbyopic persons need several different corrections according to the sight distance. A type of lens providing said corrections is the bi-focal (or multi-focal) lens, which comprises at least two clearly differentiated sectors, an upper sector for far vision and a lower sector for near vision. One of the most uncomfortable features in the bifocal lenses for wearers is the visible line dividing said sectors.

In order to minimize this problem, progressive lenses have been developed in the last decades exhibiting a continuous correcting power range to see at all distances. This is achieved by continuously varying the radius of curvature of the lens surface.

In progressive lenses, contrary to what happens in bifocal lenses, there are neither visible lines nor sudden power changes, but these advantages are obtained at the expense of increasing aberrations in the lens periphery, since it is not possible to form a progressive surface utterly devoid of optical defects in its periphery.

The progressive lenses comprise four functionally different areas: an upper area for long distance, a lower area for short distance, a transition area therebetween, and a distorted vision peripheral area.

In recent years, advances in progressive surface geometry, in software of design thereof and in lens manufacturing technology have allowed to reduce the peripheral aberrations and bringing them close to their theoretical limits.

On the other hand, given the great number of design combinations the progressive lenses may assume and the variety of conditions to be met, there is not any univocally correct solution for all the wearers in all the situations of use of the lenses. Furthermore, modifying the size of one area affects the size of the others and it alters the level of aberration.

A recent tendency in the design of progressive lenses points to lens customisation to improve the wearer's response. This is currently feasible due to the steps forward in numerical control machining and computer aided manufacturing technology.

It is known that many wearers of progressive lenses designed under "industrial" criteria, not customised, have found difficulties in adaptation to their lenses. This is due to the fact that, with a conventional system, the manufacturer offers a limited series of lenses with some optical features averaged depending upon the prescribed optical correction and the main use of the lenses (reading, outdoor activities, etc). In this context, customisation involves incorporation of the wearer's personal features into the lens design process, and it may be applied to the design of any type of lens for spectacle frame, not only to the progressive lens design.

This customisation is based upon measuring by some means the individual's eye and head movement pattern. It has been proven that the coordination of the eye and the head movements is the result of an individual behaviour, a personal strategy of vision. All types of visual behaviours have been found, from people moving their eyes a lot and their head a little, to those moving their head a lot and their eyes a little.

For example, a presbyopic person predominantly moving his/her eyes for reading will be better adapted to progressive lenses which design contains a relatively wide short distance vision area and a relatively long transition area (smoother), whereas for one individual predominantly moving his/her head lenses having a relatively narrow short distance vision area an relatively short transition area (more abrupt) will be better.

EP0880046 teaches a method of manufacturing a progressive lens in which design information relating to the shape of the frame and the habits and activities of the individual has been included. This design is carried out by means of a computer program.

WO01/62139 relates to a method of designing a lens using a movement detection system for determining the movement of the head of lens wearer while performing a series of visual exercises. Then a computer, by virtue of a calculation algorithm, provides an inference in the movement of the wearer's eyes. The data obtained are combined with the wearer's personal information for classifying him/her into a visual behaviour category. Finally, a computer application, based on predetermined relationships, selects a progressive lens in keeping with the category of the wearers visual behaviour.

SUMMARY OF THE INVENTION

With the purpose of obtaining an authentically customised lens with regard to the wearers visual behaviour while performing complex visual tasks, a first aspect of the present invention is a method for establishing the visual behaviour of a person, which comprises the steps of recording the movement of at least one of his/her eyes while performing a visual task, determining in different moments of time the relative orientation of the eye relative to the head, and determining the amount of time that the eye has been held in each orientation. This amount of time will define with enough accuracy which are the most frequent eye orientations and which are the most used lens areas for different visual tasks.

Normally, the eye orientation will be equivalent to the line of eyesight orientation, and the coordinates of the eye orientation will be the horizontal angle of the line of eyesight with regard to a reference plane and the vertical angle of the line of eyesight with regard to a reference plane. Then, the relative orientation of the eye with regard to the head will be determined through vector subtraction of the head orientation from the line of eyesight orientation.

In one embodiment of this first aspect of the invention, the amount of time that the eye has been held in each orientation is determined by grouping the records of said orientations into finite intervals and assigning to each of these intervals the amount of time that the eye has been held in the orientations contained therein.

In one preferred embodiment, the amount of time the eye has been held in each orientation is determined by grouping the records of said orientations into finite intervals and grouping the quantity of records contained in each interval.

With the above data a graph of the set of records of orientations relative to the head may be plotted wherein a first axis represents the horizontal angle of the line of eyesight with regard to a first reference plane associated with the head, and in which a second axis represents the vertical angle of the line of eyesight with regard to a second reference plane associated with the head. Said first and second axes define a vector space or plane of orientations.

In connection with said graph, it is useful to discretize the plane of orientations in finite intervals, counting the amount of orientation records contained in each interval, and plotting on the plane of orientations a three-dimensional histogram in which the height is a function of said amounts of orientation records. Another possibility is colour marking each interval which frequency is a function of its amount of orientation records. With these graphic representations one can see immediately which are the most frequent eye orientations.

The eye orientations may be further represented in different graphs according to the moments when the person moves the gaze and the moments when fixing the gaze. The latter will be the most interesting for the customised lens design.

It may be also interesting to obtain a three-dimensional combined graph in which the height is a function of the amount of time that the line of sight has been held in each discretized orientation, and the colour is a function of the amount of records to which the sight has been fixed in said orientation.

All of these graphic representations may be obtained by composing the results obtained for several different visual tasks. A movement sensing device with at least two degrees of freedom, of the electromagnetic, ultrasonic, gyroscopic or image processing type may be used for determining the head movement, and a gaze sensing device of the infrared or image processing type, with at least two degrees of freedom, may be used for determining the line of eyesight orientation.

Advantageously, said visual task comprises a series of visual exercises designed for examining the mobility of the person's head and eye when gazing at one or several different distances.

The study of the person's visual behaviour may be completed by examining his/her response to different visual tasks.

A second aspect of the present invention is a method of customisation of a lens for spectacle frame that is based on establishing the visual behaviour of the wearers spectacle frame according to what it has been set forth in the above paragraphs of this section. Said method may also comprise the step of analyzing the wearer's physical features, preferences, habits and needs.

A third aspect of the present invention is an equipment for establishing the visual behaviour of a person which comprises a device for sensing the line of eyesight orientation while performing a visual task, means for recording eye and head movement data, means for determining at different moments of time the relative orientation of the eye with regard to the head, and means for determining the amount of time the eye has been held in each orientation.

In one embodiment, said device for sensing the movement of the individual's head comprises at least two light emitting elements held on the user's head and means for sensing said light emitting elements. Preferably, said means for sensing said light emitting elements comprise at least two cameras arranged such that they can perform a stereoscopic mapping of the head.

Advantageously, the device for sensing the line of eyesight orientation comprises a displaying device with a moving light spot which the user has to follow with his/her eyes.

In one preferred embodiment, said display means comprise a screen divided into an upper half screen and a lower half screen which are at different distances from the user's eyes. The upper half screen is normally nearer the user so that he/she has to lean his/her eyes when the light spot goes through said lower half screen.

Said screen and the two cameras may be built into a measurement device that is connected with a control device, said measurement and control devices being included in a computing device that records and processes the data relating to the orientation of the user's head and eyes. Said computing system also comprises said means for determining at different moments of time the relative orientation of the eye with regard to the head, said means for determining the amount of time the eye has been held in each orientation, and a module for compressing and encoding the information recorded about the user's visual behaviour.

In one preferred embodiment the control device comprises means for determining the location of the user's eyes corneal reflex relative to the light emitting elements. The absolute position of the eyes is thus determined.

Advantageously, the control device comprises means for validating the carrying out of said visual task. If said task is not properly carried out it is repeated.

BRIEF DESCRIPTION OF THE DRAWINGS

For a better understanding of what it has been set out drawings are herein accompanied in which practical modes of embodiment are diagrammatically shown and only by way of a non-limitative example.

In the drawings.

DESCRIPTION OF PREFERRED EMBODIMENTS

An equipment 1 for carrying out a method for establishing the visual behaviour of a person according to one embodiment of the invention is described hereinbelow.

Figure 1:
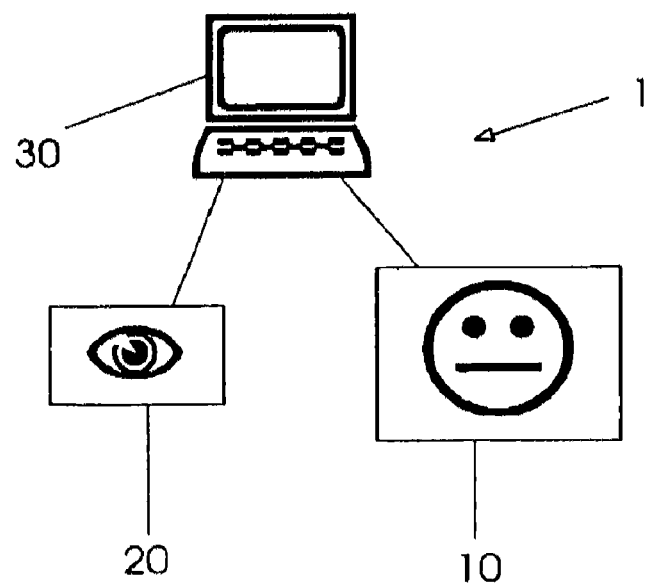
FIG. 1 is a diagram of an equipment for carrying out a method according to one embodiment of the invention.

As it may be seen from FIG. 1, the equipment 1 comprises a device 10 for sensing the movement (orientation) of the individual's head while performing a visual task, a device 20 for sensing the line of eyesight orientation while performing a visual task, and a computer or computing system 30 that records and processes data from said sensing devices. In the remainder of this disclosure, where reference is made to the orientation of the eye, it is related to the line of eyesight orientation.

Appropriate devices for these functions of sensing and recording of the eyes and head movement may be those respectively marketed under denomination "Model 504" on the part of the company ASL (Applied Science Laboratories), Bedford, Mass., and "Fastrack" on the part of the company "Polhemus", Colchester, Vt., both from the United States of America.

The object of the method is to determine in different moments of time the relative orientation of the eye with regard to the head and also the amount of time that the eye has been held in each orientation. In this context, the amount of time that the eye has been held in each orientation involves a measurement or estimate of the time that the eye has been held fixed within a finite interval of orientations grouped by proximity.

Figure 2:
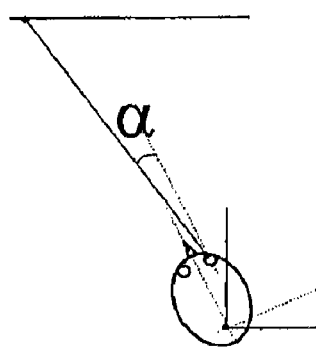
FIG. 2 is a diagrammatic representation of the determination of the horizontal angles of the head and eye orientation.
Figure 3:
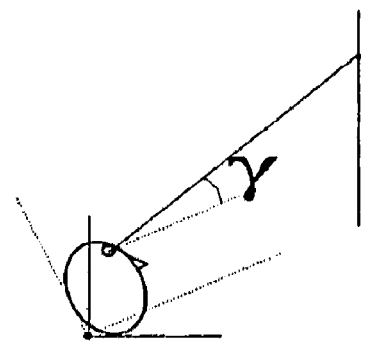
FIG. 3 is a diagrammatic representation of the determination of the vertical angles of the head and eye orientation.

Within the context of the present invention, one orientation is specified by means of two angular coordinates, a rotation coordinate or horizontal angle ALPHA ($\alpha$) of the line of eyesight with regard to a first reference plane (FIG. 2), and another one of flexion or vertical angle GAMMA ($\gamma$) of the line of eyesight with regard to a second reference plane (FIG. 3).

The relative orientation of the eye with regard to the head is calculated from the orientation of the head with regard to an external reference and the position of the point to which gaze is directed. The orientation of the head is obtained by means of the device 10 and a biomechanical model of the head-neck-trunk kinematic chain. The position of the point to which gaze is directed is obtained by means of the device 20 and an eye-head biomechanical model provides the orientation of the gaze direction. These biomechanical models are included in the calculation software of the computer 30.

The calculation of the relative orientation of the eye with regard to the head relies upon that once the position of the point to which gaze is directed and the position of the theoretical centre of rotation of the eye are known, the line of eyesight orientation may be calculated. This orientation is the vector sum of the orientation of the head and the relative orientation of the eye with regard to the head. Therefore, the relative orientation of the eye with regard to the head is calculated by the vector subtraction of the orientation of the head from the orientation of the line the eyesight.

Figure 7:
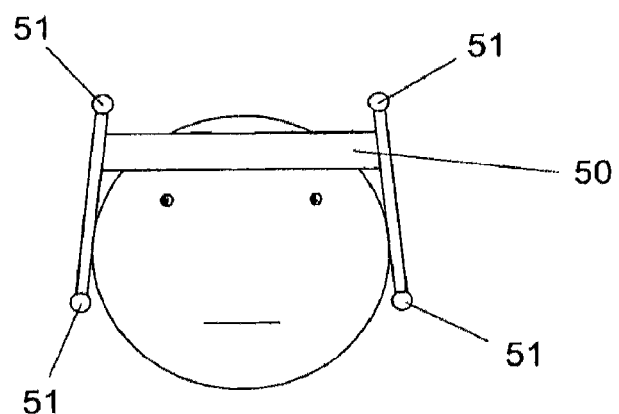
FIG. 7 is a diagrammatic illustration of a hairband provided with light emitting elements.
Figure 8:
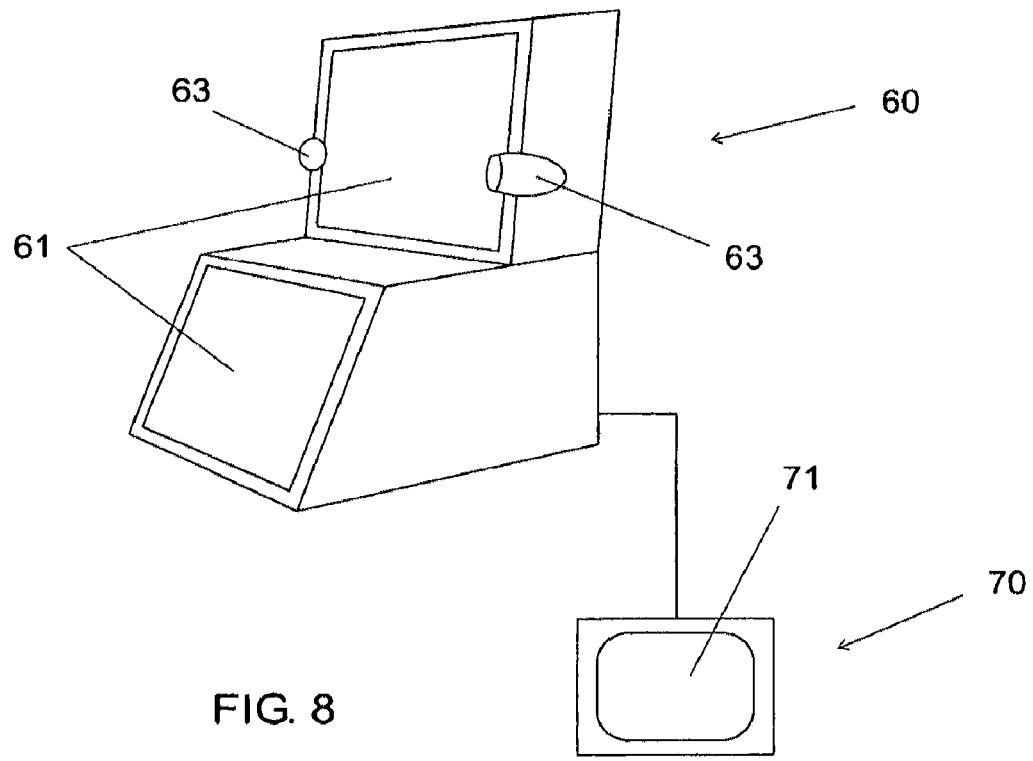
FIG. 8 is a perspective view of a camera and screen device according to one embodiment of the invention.
Figure 9:
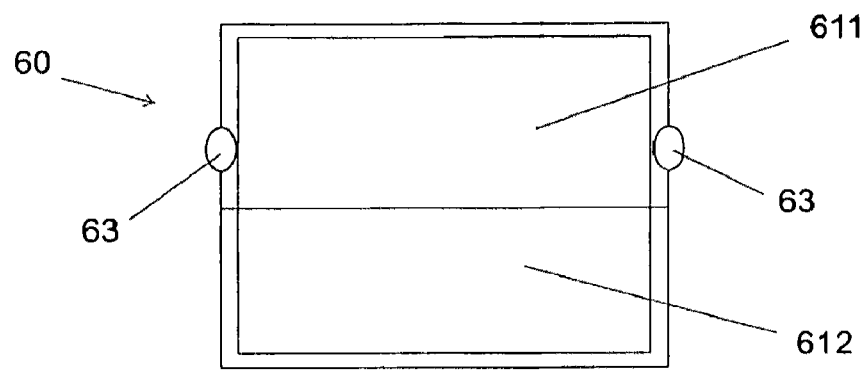
FIG. 9 is a front elevational view of the device in FIG. 8.
Figure 10:
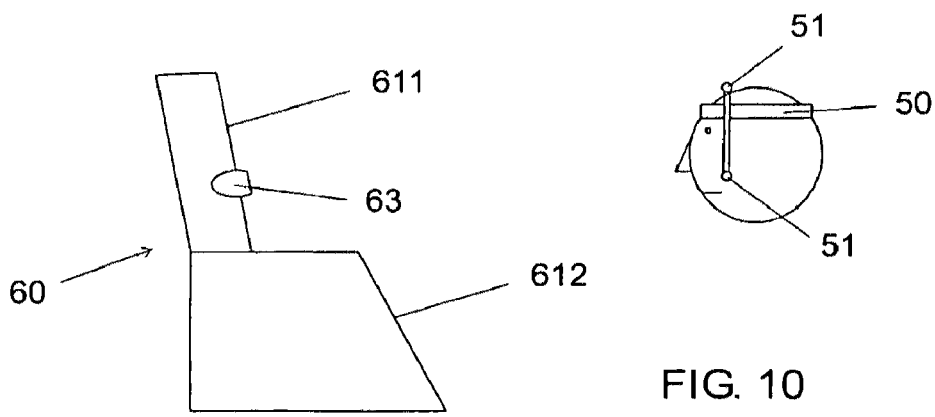
FIG. 10 is a diagrammatic illustration of the operation of the device in FIGS. 8 and 9.

An equipment for carrying out an assay that permits establishing a person's visual behaviour according to another embodiment of the invention is shown in FIGS. 7 and 10. Said equipment comprises a hairband 50 which is put on the individual's head, a measurement device 60 and a control device 70.

The hairband 50 is provided with 4 LEDs 51 which monitoring permits the individual's head movement to be tracked. The measurement device 60 comprises a computing system which records and processes data relating to the individual's head and eyes orientation. For this purpose, the measurement device 60 is further provided with a screen 61 divided into an upper half screen 611 and a lower half screen 612. Said screen 61 provides a variable visual stimulus for attracting the individual's gaze. The lower half screen 612 is offset to the individual relative to the upper half screen 611 (FIG. 10).

The measurement device 60 further includes, at each side of the upper half screen 6111 respective cameras 63 facing the individual's head detecting the light from the LEDs 51, and also its position, by parallax, when the individual is sat in a proper position in front of the screen 61 and with the hairband 50 properly put on his/her head.

The control device 70 is provided with controls for operating the equipment and it comprises a control screen 71, preferably a small sized touch screen, having the equipment functions and possibilities for establishing the individual's visual behaviour.

The operation of this equipment is as follows. The individual who is to be subjected to the assay to be carried out is told to sit at a distance of about 50 cm from the upper half screen 611 with the hairband 50 stably put on his/her brow. One will try that both the individual and the hairband are as centred as possible between the two cameras 63, which must precisely point the individual's head. The two cameras 63 provide, by parallax, a stereoscopic mapping of the individual's head.

As the assay is initiated, several indicators appear on the control screen 71 about the position of the hairband 50 relative to the measuring device 60, providing the distance, centring, height, and orientation of the head, said orientation being defined by rotation, flexion and lateral flexion. Once the correct values for these indicators have been obtained, the individual should stay in that position and fix his/her gaze on a light spot displayed on the screen 61, at eye level. One o or several images of the individual's face and eyes then appear on the control screen 71 and, by means of suitable controls of the control device 70, the position of both eyes is marked; specifically the corneal reflex of each eye is placed correctly which represents which enough approximation the position of the theoretical eye centre of rotation. The relative position of the eyes relative to the LEDs 51 is thus obtained.

The development of the assay specific task is proceeded below. Said task consists of the visual tracking, on the part of the individual, of a light spot moving tracing a continuous travel on the screen 61, said path not distinguishing between the half screens 611 and 612, that is, keeping the continuity between both half screens. The fact that the lower half screen 612 is nearer the individual than the half screen 611 permits the range of individual's line of eyesight orientations during the task to be extended, since he/she has to bow his/her head in order to follow the light spot through the lower half screen 612 more than he/she would have to do if it was a mere extension of the upper half screen 611.

During the development of this visual task, the measuring device 60 monitors the head orientation by the detection of the LEDs 51 and further detects the line of eyesight orientations since it is directed towards the light spot appearing on the screen 61 and the eye position being known. In addition, said computer system records the amount of time the eye is held in each orientation.

In the course of the visual task both the head and eye movement should be natural, that is, the individual should be relaxed so that his/her behaviour is representative of his/her natural visual strategy. There exist indicators for checking the correct carrying out and record of the visual task, such as for example a reliability indicator, ensuring the correct detection of the LEDs 51 during carrying out the task, or a robustness indicator, ensuring the correct centring of the hairband, or a naturality indicator, ensuring that the individual has not performed movements which are considered to be abnormal during carrying out the task. For giving the approval to the assay, the three indicators must present values considered to be correct.

Figure 4:
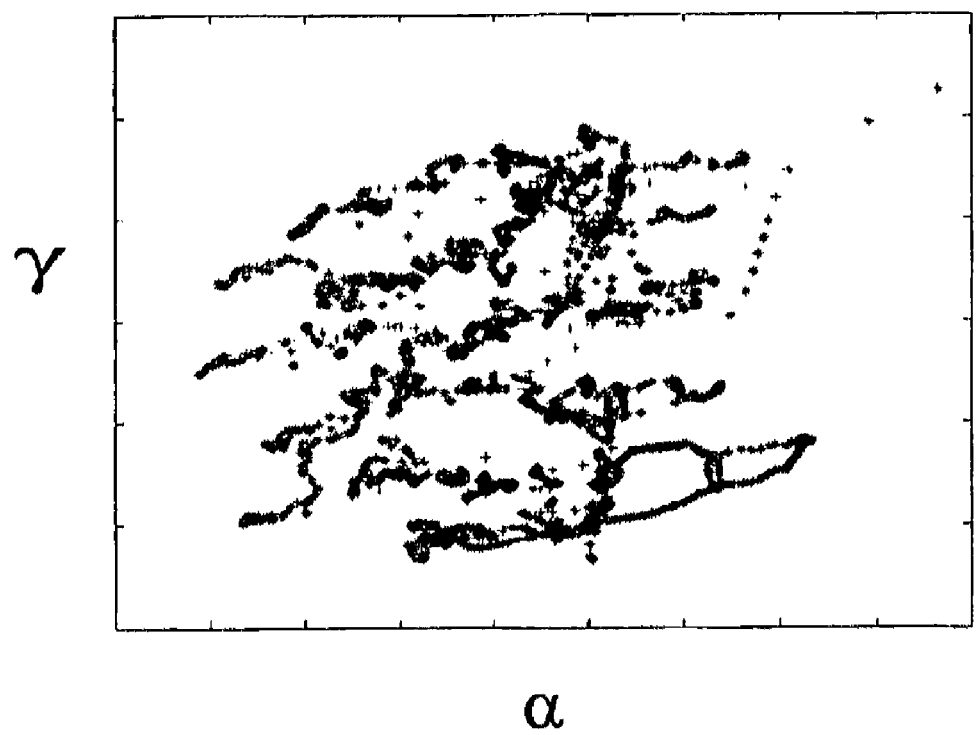
FIG. 4 is a graph of the set of orientations in a plane space of orientations.
Figure 6:
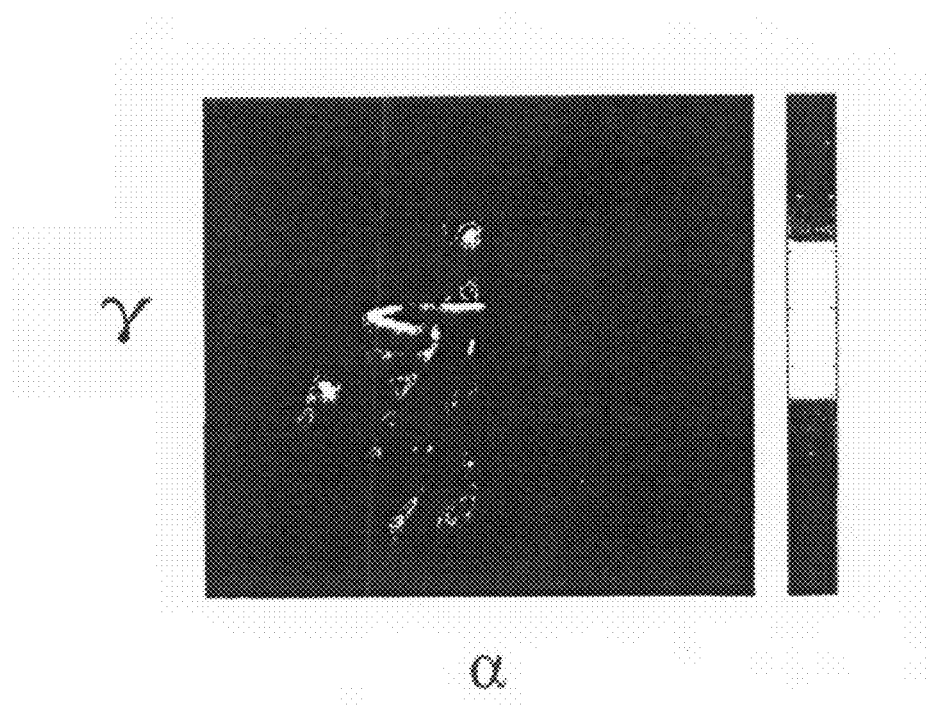
FIG. 6 is a graph of orientations with the frequency represented with a colour range.

With the time and orientation data recorded while performing a visual task, an illustrative graphic representation of the individual's visual behaviour may be obtained, which may be referred to as "vision map". For preparing a vision map, the graph of the recorded orientations (FIG. 4) is plotted first on a plane space of orientations wherein ALPHA angle is represented on the axis of abscissas and GAMMA angle is represented on the axis of ordinates. Subsequently, the plane of orientations is discretized in a set of two-dimensional finite intervals and the number of records of orientations contained in each interval is counted. This number is a frequency associated with said interval that is, it represents the time the eye has been held fixed within the interval. Finally, one colour is associated with each interval of the plane of orientations as a function of the frequency of said interval (FIG. 6). The resulting colour map is the vision map and it allows the individual's visual behaviour to be appreciated.

A specific data compression algorithm permits encoding the information contained in a vision map and transmitting it in a compact and safe way to a lens manufacturing factory. Particularly, said algorithm can provide a unique alphanumeric code which can be sent to the factory by any suitable means, for example by a telephone call, paper printed or telematically.

Figure 5:
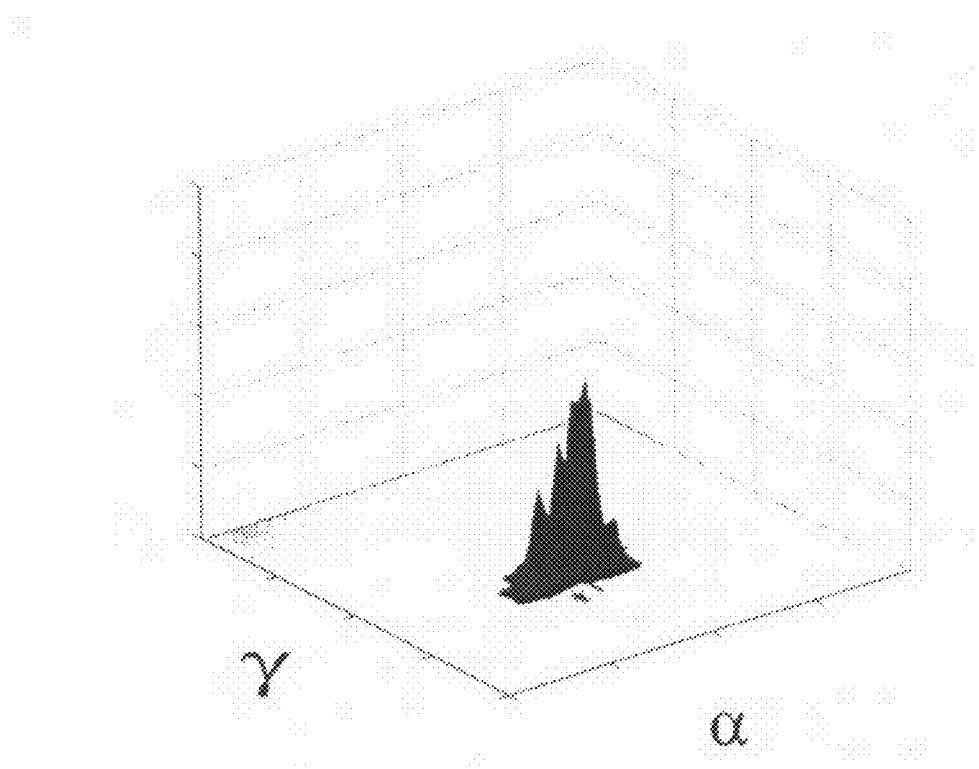
FIG. 5 is a three-dimensional histogram of the orientation frequency.

Vision maps may be obtained for a visual task or they may be composed attaching several visual tasks that, for example, comprise near, intermediate and far vision. Said visual tasks may comprise a series of suitably designed visual exercises. The vision maps may also be represented in the form of a three-dimensional histogram (FIG. 5), in which said frequency is represented in height.

Naturally the method described for constructing visual maps serves the purpose of examining any temporary series of orientations, not only those of the eyes, and it may be applied for example to head rotation and flexion.

On the other hand, during a reading task two types of visual actions may be performed by the individual, which are referred to as fixations and saccades. Fixations are the instants of time when the eye is stopped in an area of interest and the information is transmitted to the brain. Saccades are the movements carried out to direct the gaze from one fixation to another. Since fixations provide a more useful information for lens customisation, two vision maps may be obtained, one for fixations, which may be referred to as "reading areas", and another one for saccades, which may be referred to as "passing areas".

3D histogram combinations and vision maps may be also obtained. For example, a three dimensional graphic representation is useful wherein the height is a function of the amount of time that the line of sight has been held in each orientation (discrete), and the colour is a function of the number of fixations recorded for this orientation.

A process for the design of customised spectacle frames may take into account the information obtained on the visual behaviour of the frame wearer's eyes, besides other personal features. In such a process of design it may be distinguished, for example, a first level of customisation in which some features of the lenses are determined from physical characteristics such as graduation, sex, age, interpupillary distance, pantoscopic angle, astigmatism or wearer's height. In this level of customisation the wearer's preferences and habits may be also included.

With the results of said first level of customisation the most appropriate lens for the group of population in which the wearer is integrated may be determined.

Going deep into lens customisation, the design process may continue with a second level of customisation in which vision maps are determined for the wearer, according to the method described in the above paragraphs.

Based on this information a lens customised for each wearer may be designed, not only taking into account his/her physical characteristics, habits and preferences, but also his/her visual behaviour deriving from the mobility of his/her eyes and head. Particularly, the vision maps point out which are the most frequent orientations in the eyes and, therefore, which are the most used lens areas.

This customisation may be applied in an especially interesting way in the design of progressive lenses.

The invention has been described referring to several embodiments, but variations may be introduced therein by those skilled in the art and some elements may be replaced with other technically equivalent, which will also be included in the scope of protection defined by the appended claims.

For example, it is obvious that the described equipments may incorporate printing means providing printouts or images of the obtained results.

In the same manner, the control device 70 may comprise a screen 71 that is not a touch screen and including controls of any other type, or the arrangement and the number of the LEDs 51 and the cameras 63 may be any suitable for stereoscopic mapping of the head. Analogously, the screen 61 may be of any type offering the required functionalities.

Finally, it is worth mentioning that the different devices of an equipment according to the invention could be built-in in obvious ways for the skilled man.

The invention claimed is:

1. Method for establishing the visual behaviour of a person comprising:
   recording the movement of a person's head while performing a visual task;
   recording the movement of at least one of the person's eyes while performing a visual task;
   determining the orientation of the eye relative to the orientation of the head in different points in time; and
   determining the amount of time the eye has been held in each orientation;
   wherein recording the eye movement includes determining the line of eyesight orientation; making one coordinate of eye orientation the horizontal angle of the line of eyesight with regard to a reference plane and making another coordinate of eye orientation the vertical angle of the line of eyesight with regard to a reference plane;
   wherein the amount of time that the eye has been held in each orientation is determined by grouping the records of said orientations into finite intervals, assigning to each of these intervals the amount of time the eye has been held in the orientations contained therein, and grouping the amount of records contained in each interval;
   wherein the planes of orientation are broken down into finite intervals, and the number of records of orientations contained in each interval are counted and represented on a three-dimensional histogram in which the height is a function of said amounts of records of orientations, and by different colors marking each interval which frequency is a function of said amount of records of orientations.

2. Method as claimed in claim 1, wherein the relative orientation of the eye with regard to the head is determined by vector subtraction of the head orientation from the line of eyesight orientation.

3. Method for establishing the visual behaviour of a person comprising:
  recording the movement of a person's head while performing a visual task;
  recording the movement of at least one of the person's eyes while performing a visual task;
  determining the orientation of the eye relative to the orientation of the head in different points in time; and
  determining the amount of time the eye has been held in each orientation;
  wherein a set of records of relative orientations of the eye with regard to the head are plotted on a graph where the first axis of a graph is the horizontal angle ($\alpha$) of the line of eyesight with regard to a first reference plane associated with the head, and the second axis the vertical angle ($\gamma$) of the line of eyesight with regard to a second reference plane associated with the head, said first and second axes defining a vector space or plane of orientation.

4. Method as claimed in claim 1, wherein the eye orientations are represented in different graphics according to the instants when the person moves their gaze and the instants when the person is fixing their gaze.

5. Method as claimed in claim 3, wherein a third axis of the graph depicts the height of the combined three dimensional graph as a function of the amount of time that the line of sight has been held in each orientation, and amount of records to which the gaze has been fixed in said orientation is depicted in color.

6. Method as claimed in claim 3, wherein the graphic representations are obtained by compiling the results obtained for several different visual tasks.

7. Method as claimed in claim 1, wherein a movement sensing device is used to record the movement of the head; said movement sensing device having at least two degrees of freedom and having an electromagnetic, ultrasonic, gyroscopic or image processing device.

8. Method as claimed in claim 1, wherein the line of eyesight is determined by a gaze sensing device with at least two degrees of freedom, said gaze sensing device employing an infrared or image processing device.

9. Method as claimed in claim 1, wherein the visual task includes a series of visual exercises designed to examine the mobility of the person's head and eye when gazing at one or several different distances.

10. Method as claimed in claim 1, wherein a person's visual behaviour is examined by comparing either the same or different visual tasks.

11. Method of customisation of a spectacle frame lens comprising establishing the wearer's frame visual behaviour according to the method of claim 1, by testing the wearer's physical characteristics, preferences, habits, and needs.

* * * * *